US00PP23391P2

(12) United States Plant Patent
Uebelhart

(10) Patent No.: US PP23,391 P2
(45) Date of Patent: Feb. 12, 2013

(54) ***HELIOPSIS* PLANT NAMED 'SUMMER STRIPE'**

(50) Latin Name: ***Heliopsis helianthoides* var. *scabra***
Varietal Denomination: Summer Stripe

(75) Inventor: Georg G. Uebelhart, Schwarmstedt (DE)

(73) Assignee: Jelitto Staudensamen GmbH, Schwarmstedt (DE)

( * ) Notice: Subject to any disclaimer, the term of this patent is extended or adjusted under 35 U.S.C. 154(b) by 101 days.

(21) Appl. No.: 13/065,117

(22) Filed: Mar. 15, 2011

(51) Int. Cl.
*A01H 5/00* (2006.01)

(52) U.S. Cl. ..... Plt./437

(58) Field of Classification Search ..... Plt./437
See application file for complete search history.

(56) References Cited

OTHER PUBLICATIONS

Darwin Plants—Perennials 2012. Retrieved on Aug. 2, 2012. Retrieved from the Internet at <www.darwinplants.com/site/genus.asp?GenusId=Heliopsis> 2 pp.*

* cited by examiner

*Primary Examiner* — June Hwu
(74) *Attorney, Agent, or Firm* — Penny J. Aguirre

(57) ABSTRACT

A new cultivar of *Heliopsis*, 'Summer Stripe', characterized by its inflorescences with yellow ray florets with red cones, foliage that is variegated with blades that are pink, green and creamy white in color with dark green veins, its stems that are dark reddish in color, and its ability to bloom predictably as a one-year-old plant.

3 Drawing Sheets

Botanical classification: *Heliopsis helianthoides* var. *scabra.*

Variety denomination: 'Summer Stripe'.

CROSS REFERENCE TO A RELATED APPLICATION

This application is co-pending with U.S. Plant Patent Applications filed for plants derived from the same crosses in the Inventor's breeding program that are entitled *Heliopsis* Plants Named 'Summer Green' (U.S. Plant patent application Ser. No. 13/065,162) and 'Summer Pink' (U. S. Plant patent application Ser. No. 13/065,161).

BACKGROUND OF THE INVENTION

The present invention relates to a new and distinct cultivar of *Heliopsis* plant, botanically known as *Heliopsis helianthoides* var. *scabra* 'Summer Stripe' and will be referred to hereinafter by its cultivar name, 'Summer Stripe'.

'Summer Stripe' was derived from a controlled breeding program conducted by the Inventor at his nursery in Schwamstedt, Germany. The breeding program focuses on obtaining new cultivars of *Heliopsis* with novel leaf and flower colors and superior garden performance. 'Summer Stripe' was selected in 2007 by the Inventor as a single unique plant derived in 2005 from the open-pollination between unnamed plants from his breeding program with the female parent identified with accession No. Clone ex H04011 and the male parent identified with accession No. Variegated seedling GU03.

Asexual reproduction of the new cultivar was first accomplished via stem cuttings in Schwarmstedt, Germany in 2008. The characteristics of this cultivar have been determined to be stable and are reproduced true to type in successive generations.

SUMMARY OF THE INVENTION

The following traits have been repeatedly observed and are determined to be the characteristics of the new cultivar of *Heliopsis*. These attributes in combination distinguish 'Summer Stripe' as unique from and all other varieties of Heliopsis known to the inventor.

1. 'Summer Stripe' exhibits inflorescences with ray florets that are yellow in color with red cones.
2. 'Summer Stripe' exhibits foliage that is variegated with blades that are pink, green and creamy white in color with dark green veins.
3. 'Summer Pink' exhibits stems that are dark reddish in color.
4. 'Summer Pink' blooms predictably as a one-year-old plant.

'Summer Stripe' can be compared to its parents. The female parent differs from 'Summer Stripe' in having purplish green foliage without variegation. The male parent differs from 'Summer Stripe' in lacking red stems. 'Summer Stripe' can also be compared to *Heliopsis* cultivar 'Loraine Sunshine' (U.S. Plant Pat. No. 10,690). 'Loraine Sunshine' differs from 'Summer Stripe' in having green stems, yellow inflorescences with a yellow cone, and lacking the ability to flower in the first year. 'Summer Stripe' can also be compared to cultivars from the same cross 'Summer Pink' and 'Summer Green'. 'Summer Pink' differs in having inflorescences with ray florets that are yellow in color with an orange base. 'Summer Green' differs in having foliage that lacks any pink coloration.

BRIEF DESCRIPTION OF THE DRAWINGS

The accompanying colored photographs illustrate the overall appearance and distinct characteristics of the new *Heliop-*

*sis*. The photographs were taken of a one year-old plant as grown in a 3.5-liter container in a cold-story greenhouse in Lisse, the Netherlands.

Figure 1:
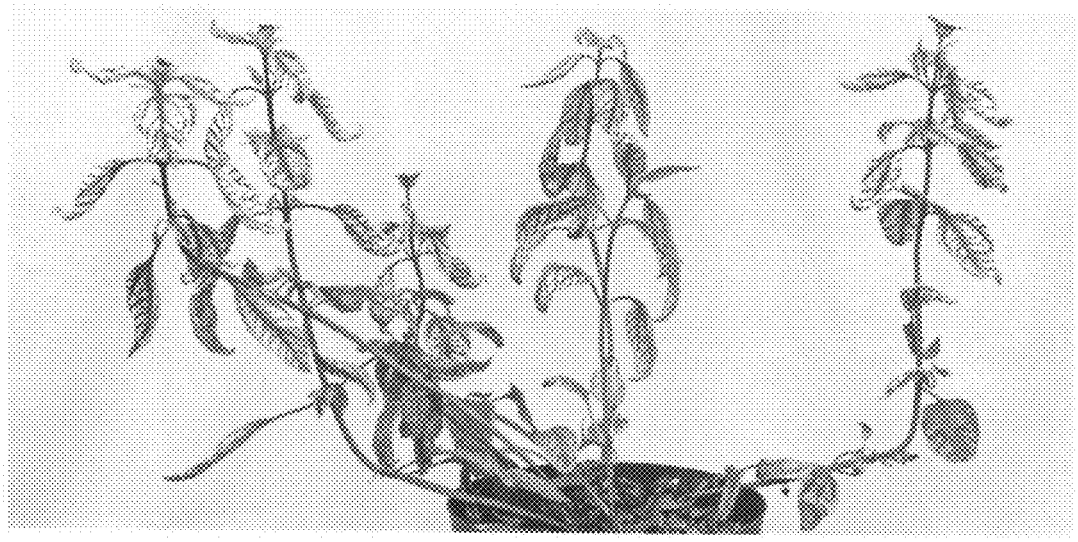

The photograph in FIG. 1 provides a side view of a plant of 'Summer Stripe'.

Figure 2:
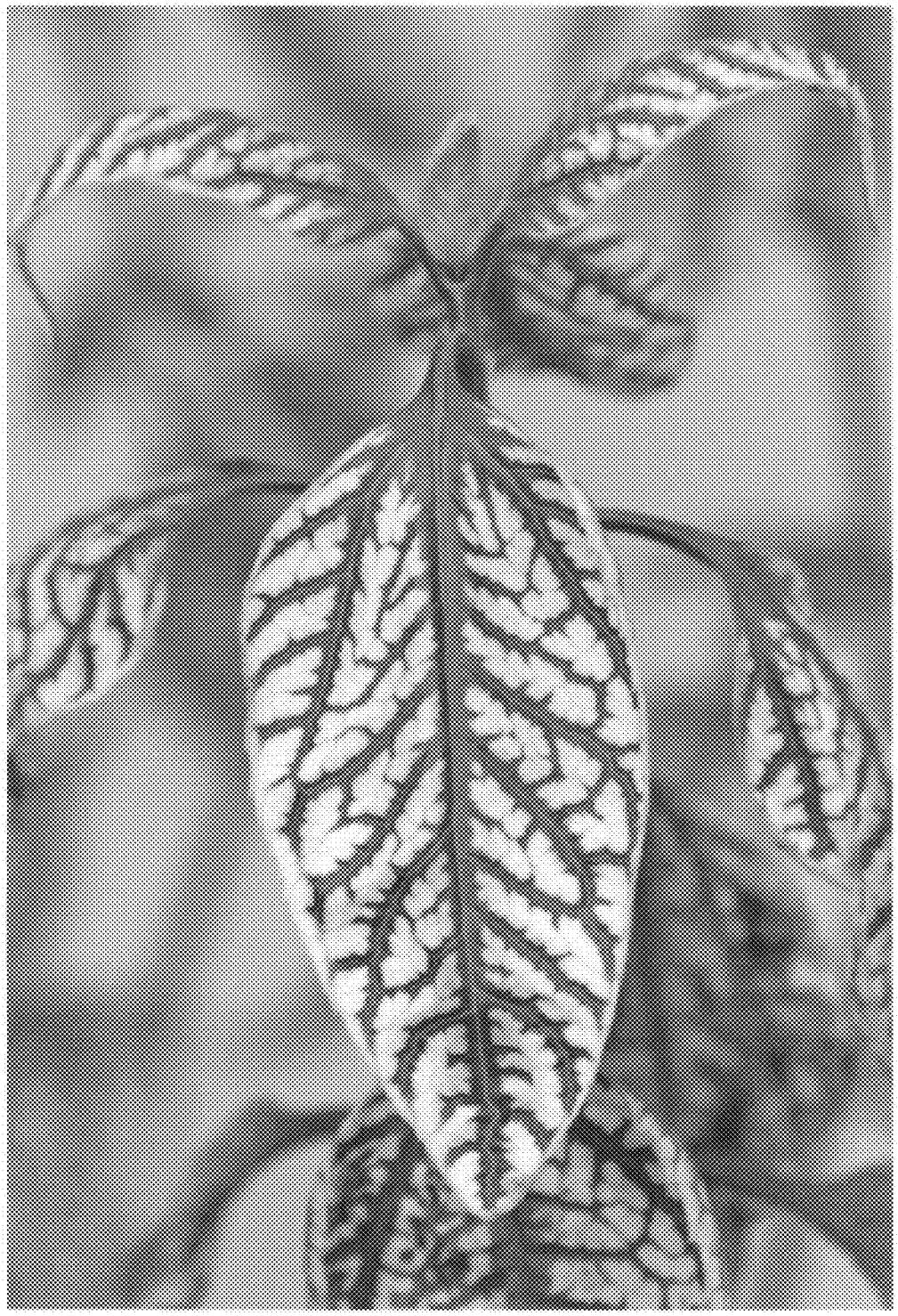

The photograph in FIG. 2 provides a close-up view of the leaves of 'Summer Stripe'.

Figure 3:
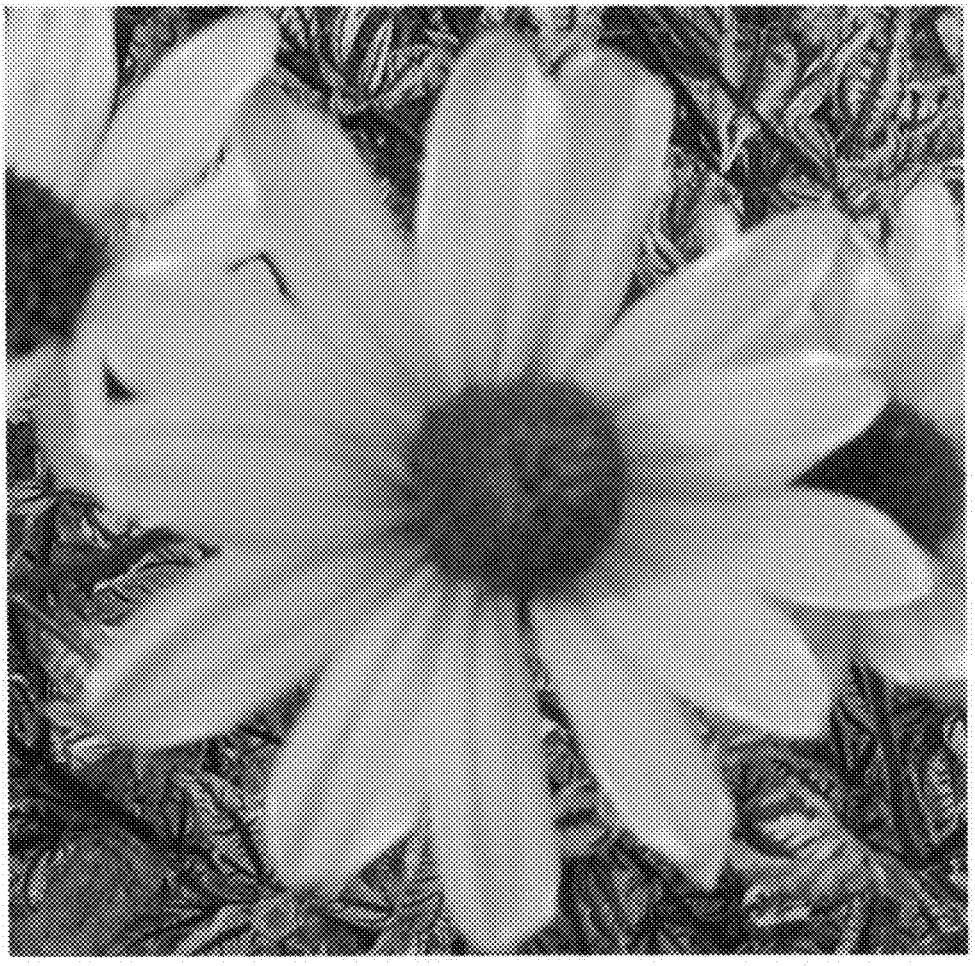

The photograph in FIG. 3 provides a close-up view of an inflorescence of 'Summer Stripe'. The colors in the photographs are as close as possible with the digital photography and printing techniques utilized and the color codes in the detailed botanical description more accurately describe the colors of the new *Heliopsis*.

DETAILED BOTANICAL DESCRIPTION

The following is a detailed description of the new cultivar collected on one year-old plants grown in 3.5 liter containers in cold-storey greenhouses in Lisse, The Netherlands in June with day temperatures ranging between 18° to 30° C. and night temperatures ranging between 8° and 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming season*.—Late spring to late summer.

*Plant habit*.—Herbaceous perennial, upright, clumping growth habit.

*Plant shape*.—Globular to broadly obovate.

*Height and spread*.—About 33.1 cm in height and 43.1 cm in width.

*Hardiness*.—U.S.D.A. Zone 4 up to temperatures as high as 35° C.

*Diseases resistance*.—No susceptibility or resistance to diseases has been observed.

*Stress resistance*.—Moderate resistance to rain, high resistance to wind.

*Root description*.—Fibrous.

Growth and propagation:

*Propagation*.—Stem cuttings and tissue culture.

*Time from cutting to flowering*.—Average of 20 weeks.

*Crop maintenance*.—No pinching or pruning required.

*Growth rate*.—Moderate, 10 cm per month.

Stem description:

*Stem shape*.—Rounded.

*Stem aspect*.—Average 30° from vertical.

*Stem strength*.—Moderate.

*Stem color*.—197A.

*Stem surface*.—Young stems slightly pubescent, hairs 1 mm in length, 155C in color, deciduous, mature stems glossy, and glabrous.

*Lateral branch length*.—Average of 34.4 cm.

*Lateral branch diameter*.—Average of 3.5 mm.

*Quantity of lateral branches*.—About 6 per plant.

*Internode length*.—Average of 5.2 cm.

*Branching*.—Freely branched with basal and lateral branches.

Foliage description:

*Leaf division*.—Simple.

*Leaf shape*.—Ovate, strongly concave.

*Leaf base*.—Attenuate.

*Leaf apex*.—Acute.

*Leaf margin*.—Finely serrate.

*Leaf venation*.—Pinnate, upper and lower surface 146A.

*Leaf attachment*.—Petiolate.

*Leaf arrangement*.—Opposite.

*Leaf surface*.—Dull, upper and lower surfaces moderately strigose, strigose hairs 0.3 mm in length, 157D in color.

*Leaf color*.—Young foliage; upper surface 155A with reticulate variegation 143A in color, lower surface a blend of 150D and 155A suffused with 75D with reticulate variegation 143B in color, mature foliage; upper surface 155A with reticulate variegation N137C, lower surface 155C suffused with 182B, reticulate variegation 143A.

*Leaf size*.—Average of 5.8 cm in length and 2.4 cm in width.

*Petiole*.—Smooth, 1.7 cm in length, 1.5 mm in diameter, upper surface; moderately glossy, 146A in color, lower surface; very glossy, 146A.

Flower description:

General description:

*Inflorescence type*.—Terminal capitulum with many disc florets, one row of ray florets, and two rows of involucral bracts.

*Flowering response*.—9 weeks.

*Rate of flowering*.—Staggered starting from the terminal inflorescence towards the youngest lateral inflorescence.

*Lastingness of inflorescence*.—About 5 Weeks, persistent.

*Fragrance*.—None.

*Quantity of inflorescences*.—1 per lateral stem, 20 per plant.

*Inflorescence buds*.—About 9 mm in depth and 1.3 cm in diameter, flattened globular in shape, 145A in color with immature involucral bracts 137A and suffused with a blend of 178A and 178B.

*Inflorescence size*.—About 1.8 cm in depth and 4.2 cm in diameter, diameter of disk about 1.4 cm, height of disk about 1.7 cm.

*Receptacle*.—Rhomboidal, about 6 mm in depth and 4 mm in diameter, 155C in color.

*Peduncle*.—Round with axial ribs, moderately strong, 197A suffused with 148A, about 14 cm in length and 2 mm in diameter, surface is slightly pubescent.

*Involucral bracts* (*phyllaries*).—Oblong in shape, 14 per inflorescence, arranged in 2 rows, broadly acute apex, broadly cuneate base, margin entire, upper surface 143A in color, lower surface 143C in color, about 1.1 mm in length, 5 mm in width, surface is dull and moderately strigose with hairs about 0.2 to 0.5 mm in length and 157D in color on upper and lower surface.

Ray florets (capitulate):

*Number*.—Average of 14.

*Arrangement*.—Rotate.

*Appearance*.—Smooth, dull.

*Shape*.—Elliptic.

*Aspect*.—Slightly upright at an angle of 10° from horizontal.

*Size*.—Average of 2 cm in length and 9 mm in width.

*Petal apex*.—Emarginate to praemorse.

*Petal base*.—Cuneate.

*Petal margins*.—Entire.

*Petal texture*.—Smooth, slightly ribbed lengthwise.

*Petal color*.—Opening; upper surface 7A, lower surface 1A, margins a blend of 6B and 7B, fully open; upper surface 14B, lower surface 7A, color not fading.

Disk florets (perfect):

*Quantity*.—Average of 100.

*Shape*.—Tubular, sympetalous with 5 lobes comprising upper 125% of floret.

*Arrangement*.—Spiral concentric towards center of disc.

*Disk lobe apex*.—Acute.

*Disk lobe margin*.—Entire.

*Petal base*.—Fused.

*Petal texture*.—Smooth, dull on inner and outer surface.

*Size*.—About 9 mm in length and 2 mm in width.

*Color*.—Bud; base 145C, mid-section 148A, apex 144C, opening; base 145C, mid-section 154C, apex 1A,; fully opened; base 145D, mid-section 152D, apex 53A.

Reproductive organs:

*Presence*.—Disk flowers are perfect, ray flowers are carpellate.

*Gynoecium*.—1 pistil per disk and ray floret, 7 mm in length, stigma decurrent and 22A in color, style 5 mm in length and a blend of 150B and 150C in color, ovary 145D in color.

*Androecium*.—5 stamen per disk floret, filament 2.4 mm in length and 145D in color, anther linear in shape, 3 mm in length, 203A in color, pollen moderate to abundant in quantity and 17B in color.

*Fruit and seed*.—No fruits or seeds observed to date.

It is claimed:

1. A new and distinct cultivar of *Heliopsis* plant named 'Summer Stripe' as herein illustrated and described.

* * * * *